US007678955B2

(12) United States Patent
Martens et al.

(10) Patent No.: US 7,678,955 B2
(45) Date of Patent: Mar. 16, 2010

(54) POROUS COMPOSITE MATERIALS HAVING MICRO AND MESO/MACROPOROSITY

(75) Inventors: Luc R. M. Martens, Meise (BE); Sebastien P. B. Kremer, Watermaal-Bosvoorde (BE)

(73) Assignee: ExxonMobil Chemical Patents Inc, Houston, TX (US)

( * ) Notice: Subject to any disclaimer, the term of this patent is extended or adjusted under 35 U.S.C. 154(b) by 874 days.

(21) Appl. No.: 11/250,166

(22) Filed: Oct. 13, 2005

(65) Prior Publication Data

US 2007/0087934 A1 Apr. 19, 2007

(51) Int. Cl.
*C07C 1/00* (2006.01)
*C07C 27/00* (2006.01)
*C07C 209/00* (2006.01)

(52) U.S. Cl. .................. 585/640; 585/639; 518/715; 564/474; 564/475; 564/479; 564/480

(58) Field of Classification Search ................ 585/639, 585/640; 518/715; 564/474, 475, 479, 480; 502/64, 67, 77–79, 208, 214
See application file for complete search history.

(56) References Cited

U.S. PATENT DOCUMENTS

| | | | |
|---|---|---|---|
| 5,098,684 | A | 3/1992 | Kresge et al. |
| 5,145,816 | A | 9/1992 | Beck et al. |
| 5,198,203 | A | 3/1993 | Kresge et al. |
| 5,304,363 | A | 4/1994 | Beck et al. |
| 2005/0013773 | A1 | 1/2005 | Shan et al. |

FOREIGN PATENT DOCUMENTS

| | | | |
|---|---|---|---|
| WO | WO 00/06492 | | 2/2000 |
| WO | WO 00/06493 | | 2/2000 |
| WO | WO 00/06494 | | 2/2000 |
| WO | WO 00/15551 | * | 3/2000 |
| WO | WO 01/17901 | | 3/2001 |
| WO | WO 2004/014798 | | 2/2004 |
| WO | WO 2004/026473 | | 4/2004 |
| WO | WO 2004/052537 | | 6/2004 |

OTHER PUBLICATIONS

S.P.B. Kremer, et al.; "Silicalite-1 Zeogrid: A New Silica Molecular Sieve with Super- and Ultra-Micropores," WILEY-VCH, Adv. Funct. Mater, vol. 12, No. 4, pp. 286-292, 2002.
S.P.B. Kremer, et al.; "Tiling Silicalite-1 Nanoslabs into 3D Mosaics," WILEY-VCH, Adv. Funct. Mater, vol. 15, No. 20, pp. 1705-1707, 2003.
A. H. Janssen et al.; "On the Shape of the Mesopores in Zeolite Y: A Three-Dimensional Transmission Electron Microscopy Study Combined with Texture Analysis," American Chemical Society, *J. Phys. Chem. B*, vol. 106, pp. 11905-11909, 2002.
C. Baerlocher et al.; "Atlas of Zeolite Framework Types," Fifth Revised Edition, 2001.
J.S. Beck et al.; "A New Family of Mesoporous Molecular Sieves Prepared with Liquid Crystal Templates," American Chemical Society, vol. 114, pp. 10834-10843, 1992.
D. Zhao et al.; "Triblock Copolymer Syntheses of Mesoporous Silica with Periodic 50 to 300 Angstrom Pores," *Science Magazine*, vol. 279, pp. 548-552, Jan. 23, 1998.
S.E. Dapurkar et al.; "Nanosized metal oxides in the mesopores of MCM-41 and MCM-48 silicates," Catalysis Today, vol. 68, pp. 63-68, 2001.
S. Hitz et al.; "Influence of Template Extraction Structure, Activity, and Stability of MCM-41 Catalysts," Journal of Catalysis, vol. 168, Article No. CA 971659, pp. 194-206, 1997.
E.P. Barrett et al.; "The Determination of Pore Volume and Area Distributions in Porous Substances. I Computations from Nitrogen Isotherms," J. Am. Chem. Soc., vol. 73, pp. 373-380, Jan. 1951.
C.T. Kresge et al.; "Ordered mesoporous molecular sieves synthesized by a liquid-crystal template mechanism," Nature, vol. 359, pp. 710-712, Oct. 22, 1992.
M. Hartmann, "Hierarchical Zeolites: A Proven Strategy to Combine Shape Selectivity with Efficient Mass Transport," Angew. Chem Int. Ed., vol. 43, pp. 5880-5882, 2004.
S. van Donk et al.; "Generation, Characterization, and Impact of Mesopores in Zeolite Catalysts," Catalysis Reviews, vol. 45, No. 2, pp. 297-319, Marcel Dekker, Inc., 2003.
Y. Liu et al.; "Steam-Stable Aluminosilicate Mesostructures Assembled from Zeolite Type Y Seeds," American Chemical Society, vol. 122, pp. 8791-8792, 2000.
Y. Tao et al.; "ZSM-5 Monolith of Uniform Mesoporous Channels," American Chemical Society, vol. 125, pp. 6044-6045, 2003.
D. Zhao et al.; "Nonionic Triblock and Star Diblock Copolymer and Oligomeric Surfactant Syntheses of Highly Ordered, Hydrothermally Stable, Mesoporous Silica Structures," American Chemical Society, vol. 120, pp. 6024-6036, 1998.

* cited by examiner

*Primary Examiner*—In Suk Bullock
(74) *Attorney, Agent, or Firm*—Kevin M. Faulker; David M. Weisberg; Frank E. Reid

(57) ABSTRACT

A composite material comprises: (a) a porous crystalline inorganic oxide material comprising a first framework structure defining a first set of uniformly distributed pores having an average cross-sectional dimension of from 0.3 to less than 2 nanometers and comprising a second framework structure defining a second set of uniformly distributed pores having an average cross-sectional dimension of from 2 to 200 nanometers and (b) a co-catalyst within the second set of pores of the porous crystalline inorganic oxide material (a).

6 Claims, No Drawings

POROUS COMPOSITE MATERIALS HAVING MICRO AND MESO/MACROPOROSITY

FIELD OF THE INVENTION

This invention relates to porous composite materials having micropores and meso- or macropores, to a method of making such materials and to their use in organic conversion reactions.

BACKGROUND OF THE INVENTION

Zeolites and zeolite-like materials are oxides of one or more elements selected from silicon, aluminum, phosphorus, and other metal atoms and contain pores and cavities having a size that may range from a few angstroms to about 2 nanometers. In this application, the terms micropore, microporous and all their derivatives refer collectively to pores having a diameter of less than 2 nanometers.

Zeolites and zeolite-like materials are characterized by their chemical composition (e.g., Si:Al atomic or molar ratios), as well as their crystal framework connectivity, conveniently described by a topological model. For a given chemical composition, an infinite number of theoretical structures is possible. Zeolites with over 130 different topologies have been synthesized, characterized and assigned a three letter code as mentioned in the *Atlas of Zeolite Framework Types*, 5th edition, Elsevier, London, England (2001).

Zeolites and zeolite-type materials are widely used in separation processes (ion exchange, selective sorption). In their acid form, zeolites and zeolite-like materials are acid catalysts, due to the combination of their strong acidity and molecular size- and shape-selectivity. Such catalytic reactions normally take place in the pores and cavities of zeolites and zeolite-type materials but intra-particle diffusion limitations and pore blocking can prevent accessibility to a large number of catalytic sites. Also, it is often desirable to use a co-catalyst in order to tailor the catalytic activity of zeolites and zeolite-type materials to the particular use. The presence of the co-catalyst in close proximity of the catalytic sites is typically required for optimal performance. However, pore sizes of a few angstroms or even a few nanometers make it very difficult to synthesize materials where co-catalysts are in close proximity to the active sites of zeolites or zeolite-type materials.

One way to increase intra-particle diffusion is to reduce the size of the zeolite or zeolite-type crystals. Various methods have been described to make small crystal size molecular sieves (see, for example, International Patent Publication Nos. WO 00/06492, WO 00/06493, and WO 00/06494). However, the colloidal behavior of very small particles makes them difficult to recover and handle, especially on an industrial scale. Moreover, reducing crystal size does not address the issue that the microporous nature of zeolite or zeolite-like materials makes it difficult to introduce co-catalysts in close proximity to the catalytically active sites.

Another way to increase intra-particle diffusion is to increase the pore and cavity size of the molecular sieve. The synthesis of ordered mesoporous aluminosilicate catalysts; with pores of about 2 nanometers or larger, such as MCM-41, has been reported in the literature (see, for example, Kresge et al., *Nature*, 1992, 359, 710; Beck et al, *J. Am. Chem. Soc.* 1992, 114, 10834; D. Zhao et al., *Science*, Vol. 279, pp. 548-552, 1998). In the context of the present invention, "mesopores" refers to pores having a diameter of from 2 to 50 nanometers and "macropores" refers to pores having a diameter of greater than 50 nanometers.

However, while such mesoporous materials offer good diffusion properties, they frequently lack the strong acidity of their microporous analogues, and, of course, the desirable shape selectivity of microporous zeolite and zeolite-like materials is lost. Therefore, various strategies have been developed to modify the physical and chemical properties of mesoporous materials. For example, U.S. Pat. No. 5,145,816 discloses post-synthesis functionalization of MCM-41 type materials. In addition, it is known to encapsulate metal oxides in the mesopores of MCM-41 materials, see, for example, Dapurkar et al., *Catalysis Today*, 68 (2001), 63-68.

It is also known to introduce zeolite-type microporous structure in such mesoporous materials (see, for example, International Patent Publication Nos. WO 00/15551, WO 01/17901, WO 2004/026473, and WO 2004/052537). Another method for making crystalline materials with mesopores and zeolite-type micropores is to generate mesopores by steaming or acid-leaching microporous zeolites (see, for example, A. H. Janssen et al., *J. Phys. Chem. B* (2002) Vol. 106, pp. 11905-11909; S. van Donk et al. *Catal. Rev.* (2003) Vol. 45, p. 297). Yet another method has been described by growing aluminosilicate crystals in a mesoporous support (US Patent Application Publication No. 2005/0013773 and Y. Tao et al., *J. Am. Chem. Soc.* (2003), Vol. 125, pp. 6044-6045) or by growing zeolite crystals in the presence of nanoscale carbon black particles, followed by carbon combustion (see, for example, M. Hartmann, *Angew. Chem. Int. Ed.* (2004), Vol. 43, 5880-5882).

One of the drawbacks of the above-mentioned methods is that it is quite difficult to control simultaneously the micropore size/shape distribution and the mesopore size/shape distribution in the materials, to achieve optimal catalytic performance and intra-particle diffusion. For this reason, several research groups have been looking for other methods of making crystalline materials having mesopores of uniform size together with zeolite or zeolite-like micropores. One such method involves starting from very small zeolite nuclei (often referred to as "seeds"), having a size in the order of 1 nanometer and assembling them hierarchically around regularly sized and shaped templates, said templates having a size in the range of from about 2 nanometers to about 100 nanometers, preferably from about 2 nanometers to about 50 nanometers. For example, Y. Liu et al. (*J. Am. Chem. Soc.* (2000), Vol. 122, pp. 8791-8792) disclose the assembly of a hexagonal aluminosilicate structure from seeds that would normally nucleate the crystallization of faujasitic zeolite type Y. The seeds are heated in the presence of cetyltrimethylammonium bromide to form the mesoporous hexagonal structure.

International Patent Publication No. WO 2004/014798 discloses a method of producing a microporous and mesoporous aluminosilicate material having a silica to alumina molar ratio of 2 to 50, preferably 4 to 10, in which a precursor solution of a faujasitic zeolite containing tetramethylammonium cations is formed, the precursor solution is aged and is then mixed with a solution of a cationic surfactant, such as a cetyltrimethylammonium compound. The resultant gel is then crystallized at 20 to 200° C. for between 30 minutes and 7 days.

S. P. B. Kremer et al. (Ph. D. thesis, Katholieke Universiteit Leuven, February 2004; *Adv. Funct. Mater.* (2002) Vol. 12, No. 4, pp. 286-292; *Adv. Mater.* (2003), Vol. 15, No. 20, pp. 1705-1707) disclose assembling "nanoslabs" to form materials having regular sized mesopores and micropores, referred to as "zeotiles" or "zeogrids". The nanoslabs used in this work are building blocks that would normally generate zeolites having the Silicalite-1 (MFI) framework type. The nanoslabs were formed by hydrolysis of TEOS in a concentrated aqueous TPAOH solution. The nanoslabs were assembled into zeotiles or zeogrids, by precipitation in the presence of cetyltrimethylammonium bromide (CTAB), dodecyltrimethylammonium bromide (DCTAB) or Pluronic P123 triblock copolymer under acidic conditions. After removal of CTAB, DCTAB, or Pluronic P123, an exceptionally open and ordered mesopore network, made of a zeolite-type material, was obtained.

SUMMARY OF THE INVENTION

In one aspect, the invention resides in a composite material comprising:
(a) a porous crystalline inorganic oxide material comprising a first framework structure defining a first set of uniformly distributed pores having an average cross-sectional dimension of from 0.3 to less than 2 nanometers and comprising a second framework structure defining a second set of uniformly distributed pores having an average cross-sectional dimension of from 2 to 200 nanometers; and
(b) a co-catalyst within said second set of pores of said porous crystalline inorganic oxide material.

In a further aspect, the invention resides in a method of making a porous, composite material, the method comprising:
(a) providing a porous crystalline inorganic oxide material comprising a first framework structure defining a first set of micropores and comprising a second framework structure defining a second set of mesopores or macropores;
(b) introducing a co-catalyst precursor in the second set of pores of said inorganic oxide material; and
(b) transforming the co-catalyst precursor into a co-catalyst.

In yet a further aspect, the invention resides in a method of making a porous, composite material, the method comprising:
(a) providing a porous crystalline inorganic oxide material comprising a first framework structure defining a first set of micropores and comprising a second framework structure defining a second set of mesopores or macropores, wherein said micropores are occupied by a structure-directing agent, and said second set of pores are substantially free of structure-directing agent;
(b) introducing a co-catalyst precursor in the second set of pores of said inorganic oxide material;
(c) transforming the co-catalyst precursor into a co-catalyst; and
(d) removing the structure directing agent from the micropores of the inorganic oxide material.

Conveniently, (b) and (c) are carried out simultaneously.

Alternatively, (b) is carried out before (c) or (c) is carried out before (b).

Conveniently, said co-catalyst is selected from one or more of (a) at least one metal oxide different from said inorganic oxide material, (b) a phosphorus-containing compound, (c) a hydrogenation-dehydrogenation component, and (d) a microporous molecular sieve having a framework structure different from said first framework structure.

Conveniently, the pores of said second set of uniformly distributed pores have an average cross-sectional dimension of from greater than 50 to 200 nanometers. More preferably, the pores of said second set of uniformly distributed pores have an average cross-sectional dimension of from 2 to 50 nanometers.

In one embodiment, the inorganic oxide material is selected from silica, alumina, aluminosilicates, aluminogermanates, silicoaluminogermanates, silicoaluminophosphates, aluminophosphates, and metal substituted forms thereof. Preferably, the inorganic oxide material is an aluminosilicate or a silicoaluminophosphate.

Preferably, said first framework structure is an MFI, MEL, MTW, BEA, FER, TON, MTT, MFS, MOR, ITE, CHA, AEI, or intergrown CHA/AEI framework type.

Preferably, said second framework structure is of lamellar, hexagonal, or cubic configuration.

In still a further aspect, the invention resides in a process for converting a starting material into a product, the process comprising contacting the starting material with a catalyst comprising a porous, composite material as described herein.

In one embodiment, the process comprises the conversion of an organic oxygenate to olefins and the co-catalyst is at least one metal oxide capable of extending the life of the catalyst and/or of combusting hydrogen produced as a by-product of the process.

In another embodiment, the starting material is synthesis gas and the co-catalyst is at least one metal oxide capable of catalyzing the conversion of synthesis gas to methanol.

In another embodiment, the process comprises the production of alkylamines by the reaction of organic oxygenates with ammonia.

DESCRIPTION OF THE EMBODIMENTS

The present invention relates to the composition and synthesis of composite materials which comprise a porous crystalline inorganic oxide material having both meso- and/or macroporosity and microporosity and which also incorporate a co-catalyst in their meso- or macroporous structure. The present invention also relates to the use of such composite materials as catalysts in chemical and petrochemical processes, particularly the production of olefins from organic oxygenates, such as methanol and/or dimethyl ether, and in the direct conversion of synthesis gas (also referred to as syngas) to olefins.

Porous Crystalline Inorganic Oxide Material

The porous crystalline inorganic oxide material employed in the present composite structure comprises a first framework structure defining a first set of uniformly distributed pores having an average cross-sectional dimension of from 0.3 to less than 2 nanometers and a second framework structure defining a second set of uniformly distributed pores having an average cross-sectional dimension of from 2 to 200 nanometers.

Generally, the first set of uniformly distributed pores has an average cross-sectional dimension of from 0.3 to 1 nanometer and, where the composite material is to be used as a catalyst in the conversion of oxygenates or syngas to olefins, first set of pores preferably has an average cross-sectional dimension of from 0.3 to 0.5 nanometer. The topology of the first framework structure can vary widely but typically will be such that the first framework structure is of the MFI, MEL, MTW, BEA, FER, TON, MTT, MFS, MOR, ITE, CHA, AEI, or intergrown CHA/AEI framework type as defined in the *Atlas of Zeolite Framework Types,* 5th edition, Elsevier, London, England (2001). Where the composite material is to be used as a catalyst in the conversion of oxygenates or syngas to olefins, the first framework structure is preferably of the CHA, AEI, or intergrown CHA/AEI type. Where the composite material is to be used as a catalyst in the reaction of oxygenates with ammonia to produce alkylamines, the first framework structure is preferably of the MFI, MOR CHA, AEI, or intergrown CHA/AEI type.

Preferably, the second set of uniformly distributed pores has an average cross-sectional dimension of from 2 to 50 nanometers, and hence is in the mesoporous range. Alternatively, the second set of uniformly distributed pores is in the macroporous range and has an average cross-sectional dimension of from greater than 50 to 200 nanometers. In another embodiment, the porous crystalline material has mesopores and macropores, in addition to the micropores.

The second set of pores is uniformly distributed, which means that mesopores and/or macropores occur throughout the composite material. In this respect, the second set of pores is different from meso- or macropores that typically occur in zeolitic materials and that are often referred to as stacking faults. The presence of mesopores and macropores throughout the composite material can be verified experimentally by measuring the pore volume of the composite material, which typically will be larger than 0.1 ml/g, preferably larger than 0.2 ml/g, such as 0.5 ml/g or more. Typically, microporous materials with stacking faults have pore volumes of 0.1 ml/g or less. Also, the mesopores and/or macropores have a fairly narrow size distribution, such that at least 90% by volume of all meso- and macropores are desirably within 50%, preferably within 30%, and advantageously within 20% of the average meso- and/or macropore size.

In one embodiment of the invention, the meso- and/or macropores can have a high degree of order, such as a lamellar, hexagonal, or cubic structure. However, this is not a requirement of the invention. Examples of known mesoporous framework structures suitable for use as the second framework structure include MCM-41, which is described in detail in U.S. Pat. No. 5,098,684; MCM-48, which is described in detail in U.S. Pat. No. 5,198,203; MCM-50, which is described in detail in U.S. Pat. No. 5,304,363 and SBA-15, which is described in detail in Zhao, D., et al., *Science* 279 548 (1998). In one embodiment, the second framework structure defining the second set of uniformly distributed pores may have one of the aforementioned mesoporous framework structures.

The presence of the different types of pores in the crystalline material of the invention can be determined by nitrogen adsorption. The t-plot method provides the micropore volume, whereas the BJH method provides the mesopore size distribution and volume (see E. P. Barrett, L. G. Joyner, P. P. Halenda, "The determination of pore volume and area distributions in porous substances. I Computation from nitrogen isotherms", J. Am. Chem. Soc. 1951, 73, 373). Macroporosity is better assessed using transmission electron microscopy or mercury porosimetry.

The composition of inorganic oxide material employed in the present composite structure is not narrowly defined but is typically selected from silica, alumina, aluminosilicates, aluminogermanates, silicoaluminogermanates, silicoaluminophosphates, aluminophosphates, and metal substituted forms thereof. Preferably, the inorganic oxide material is an aluminosilicate, a silicoaluminophosphate, or a metal substituted form thereof.

Method of Making the Porous Crystalline Inorganic Oxide Material

The porous crystalline material can be produced by any of the known methods for producing materials with a combination of microporosity and meso/macroporosity.

For example, one suitable method is that described in International Patent Publication WO 2004/014798, the entire contents of which are incorporated herein by reference. In this method, a faujasitic zeolite precursor solution is first prepared by dissolving an aluminum source, such as aluminum hydroxide, in an aqueous solution of tetramethylammonium hydroxide, mixing the resultant solution with a silica source and then aging the mixture at a temperature of 4° C. to 150° C. for a time between 10 minutes to 7 days such that the formation of faujasite crystals is not detected. The faujasitic zeolite precursor solution is then mixed with a solution of a cationic surfactant, such as a cetyltrimethylammonium compound, and the resultant gel is subsequently crystallized at 20° C. to 200° C. for between 30 minutes and 7 days. The crystalline product is recovered, for example, by filtration, washed, dried, and then calcined to remove the organic material and produce an aluminosilicate material exhibiting both microporosity and mesoporosity. By using appropriate chemical leaching procedure (see, e.g., by S. Hitz, R. Prins, Influence of template extraction on structure, activity, and stability of MCM-41 catalysts, J. Catal. 1997, 168, 194.), it is possible to remove selectively the organics present in the mesopores while the organics in the micropores remain.

An alternative approach involves the clear solution synthesis of nanometer-sized microporous silicate crystals, typically having an MFI framework structure, followed by the assembly of these crystals into mesoporous structures using surfactant templates or into macroporous structures using macrotemplates, such as polystyrene spheres. In the clear solution synthesis of the MFI silicate termed Silicalite-1, tetraethylorthosilicate (TEOS) is hydrolyzed in an aqueous solution of tetrapropylammonium hydroxide (TPAOH) having a sufficiently high TPAOH concentration to inhibit silica polymerization and thereby prevent formation of the gel phase normally involved in such syntheses. The resulting solution is then allowed to crystallize and, depending on the time and temperature of the crystallization, the product can be either nano-sized zeolite platelets having a length of about 2-4 nm and a thickness of 1-2 nm, generally termed "Silicalite-1 nanoslabs", or subcolloidal zeolite crystals having a particle size of about 25-100 nm.

Zeolite nanoslabs can be linked through their corners, edges, or faces following the pattern imposed by interaction with a template, such as a surfactant or triblock copolymer, to form layered or grid-like structures in which mesoporosity is exhibited between the layers or within the interstices of the grid and microporosity is exhibited within the layers or within the walls of the grid.

Suitable surfactants include quaternary ammonium or phosphonium ions of the formula

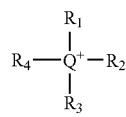

wherein Q is nitrogen or phosphorus and wherein at least one of $R_1$, $R_2$, $R_3$ and $R_4$ is aryl or alkyl of from 6 to about 36 carbon atoms, e.g., —$C_6H_{13}$, —$C_{10}H_{21}$, —$C_{16}H_{33}$-and —$C_{18}H_{37}$ or combinations thereof, the remainder of $R_1$, $R_2$, $R_3$ and $R_4$ being selected from the group consisting of hydrogen, alkyl of from 1 to 5 carbon atoms and combinations thereof. The compound from which the above quaternary ammonium or phosphonium ion is derived may be, for example, the hydroxide, halide, or silicate. A preferred surfactant is cetyltrimethylammonium hydroxide.

Suitable triblock copolymers are the poly(ethylene oxide)-poly(propylene oxide)-poly(ethylene oxide) triblock copolymers known as PEO-PPO-PEO or $(EO)_x$-$(PO)_y(EO)_z$, of the type such as those described especially by Zhao et al. in *The Journal of the American Chemical Society*, Vol. 120, pp. 6024-6036 (1998), and sold under the generic brand name PLURONIC® by BASF.

Typically, the assembly of the nanoslabs into layered or grid-like structures is achieved by adding the surfactant or triblock copolymer in powder form or as a solution, such as an aqueous solution, to a stirred suspension of the nanoslab particles in a liquid, for example, the mother liquor from the crystallization process. Depending on the conditions and mode of addition of the template, a precipitate of the desired layered or grid-like product is formed immediately on addition of the template or after allowing the mixture to stand at 60° C. to 120° C., with or without stirring for up to 96 hours. The template used to assemble the nanoslabs into a layered or grid-like structure can then be removed by leaching, for example, with a mixture of ethanol and acetic acid, whereas the template used to produce the zeolite nanoslabs, for example, TPAOH, can be removed by calcination at a temperature of 300° C. to 600° C. in air or an inert atmosphere.

More information on the use of zeolite nanoslabs to produce materials exhibiting a combination of microporosity and mesoporosity can be found in S. P. B. Kremer et al. Ph. D. thesis, Katholieke Universiteit Leuven, February 2004; *Adv. Funct. Mater.* (2002) Vol. 12, No. 4, pp. 286-292; *Adv. Mater.* (2003), Vol. 15, No. 20, pp. 1705-1707, the entire contents of which are incorporated herein by reference.

One known method for producing materials with microporosity and macroporosity involves self-assembly of subcolloidal zeolite crystals into a macroporous structure. For example, Silicalite-1 crystals having a diameter between 30 and 80 nm can be suspended in ethanol and then the suspension can be formed into a grid-like pattern by spreading a layer of the suspension on a support, such as a silicon wafer, and then imprinting the desired pattern in the layer. Upon evaporation of the ethanol, the crystals self-assemble into a film with the imprinted pattern, which is retained after calcination. Macroporous Silicalite-1 has also been obtained by infiltrating a suspension of subcolloidal crystals into porous polystyrene spheres having a diameter of the order of 300 nm, followed by calcination to remove the polystyrene macrotemplate. Self-standing Silicalite-1 membranes with a thickness of at least 20 nm have also been produced by dip-coating a suspension of subcolloidal crystals on a metal support, followed by drying, compression at $10^8$ Pa, and calcination.

Cocatalyst

In the composite material described herein, at least one cocatalyst is provided in the meso- or macropores of the second framework structure. The nature and composition of the cocatalyst can vary widely but, generally, is selected from one or more of (a) at least one metal oxide different from said inorganic oxide material, (b) a phosphorus-containing compound, (c) a hydrogenation-dehydrogenation component, and (d) a microporous molecular sieve having a framework structure different from said first framework structure.

Where the composite material is intended for use as a catalyst in the conversion of oxygenates to lower olefins, a suitable metal oxide for use as the co-catalyst is an oxide of at least one metal selected from Groups 2, 3, and 4 of the Periodic Table of Elements, wherein said metal oxide has an uptake of carbon dioxide at 100° C. of at least 0.03, and typically at least 0.035, mg/m² of the metal oxide. Thus it has been found that such metal oxides enhance the olefin yield and/or the lifetime of the catalyst when used in oxygenate conversion. In addition, the resultant catalyst composition tends to be more propylene selective and to yield lower amounts of unwanted ethane and propane, together with other undesirable compounds, such as aldehydes and ketones, specifically acetaldehyde.

In order to determine the carbon dioxide uptake of a metal oxide, a Mettler TGA/SDTA 851 thermogravimetric analysis system under ambient pressure is conveniently employed. A sample of the metal oxide sample is initially dehydrated in flowing air to about 500° C. for one hour. The temperature of the sample is then reduced in flowing helium to 100° C. After the sample has equilibrated at the desired adsorption temperature in flowing helium, the sample is subjected to 20 separate pulses (about 12 seconds/pulse) of a gaseous mixture comprising 10-weight % carbon dioxide with the remainder being helium. After each pulse of the adsorbing gas, the metal oxide sample is flushed with flowing helium for 3 minutes. The increase in weight of the sample in terms of mg/mg adsorbent based on the adsorbent weight after treatment at 500° C. is the amount of adsorbed carbon dioxide. The surface area of the sample is measured in accordance with the method of Brunauer, Emmett, and Teller (BET) published as ASTM D-3663 to provide the carbon dioxide uptake in terms of mg carbon dioxide/m² of the metal oxide.

The most preferred Group 2 metal oxide is a magnesium oxide (MgO), either alone or in combination with a Group 3 metal oxide, such as yttrium oxide, lanthanum oxide, scandium oxide, or a mixture thereof.

Preferred Group 3 metal oxides include oxides of scandium, yttrium and lanthanum, and preferred oxides of the Lanthanide or Actinide series metals include oxides of cerium, praseodymium, neodymium, samarium, europium, gadolinium, terbium, dysprosium, holmium, erbium, thulium, ytterbium, lutetium and thorium. The most preferred oxides are scandium oxide, lanthanum oxide, yttrium oxide, cerium oxide, praseodymium oxide, neodymium oxide and mixtures thereof, particularly mixtures of lanthanum oxide and cerium oxide.

Preferred Group 4 metal oxides are the oxides of zirconium and/or hafnium, either alone or in combination with a Group 2 (for example magnesium, calcium, strontium, and barium) and/or a Group 3 metal (including the Lanthanides and Actinides) oxide (for example, yttrium, scandium and lanthanum). The most preferred Group 4 metal oxide is zirconium oxide, either alone or in combination with calcium oxide, barium oxide, lanthanum oxide, and/or yttrium oxide. Particularly preferred is hydrated zirconia which has been hydrothermally treated at a temperature of at least 80° C., preferably at least 100° C for at least 1 hour, such as at least 8 hours.

Another metal oxide cocatalyst useful when the composite material is used in the conversion of oxygenates to lower olefins is a mixed metal oxide that exhibits oxidation/reduction functionality under the conditions of the conversion since such mixed metal oxides are found to reduce the amount of undesirable hydrogen produced as a by-product of the process. Suitable mixed metal oxides comprise a mixed oxide of a transition metal, usually of Series 4, 5, or 6 of the Periodic Table, with the metals of Series 4 being preferred as the essential component of the oxide composition. In preferred catalyst compositions, at least two oxides of transition metals from Series 4 and 5 will be present; in most cases it suffices to use transition metals from Series 4 and 5, with preference given to transition metals of Groups 5, especially titanium and vanadium, Group 6, especially chromium or molybdenum, and Group 8, especially iron, cobalt, or nickel with cobalt or nickel being preferred. Other metal oxides may be used in these mixed oxide compositions, including oxides of metals of Group 4 including zirconium, and Group 2, especially magnesium, calcium, or barium. Group 3 (Rare Earth) metal oxides may also be present, for example, scandium oxide, lanthanum oxide, yttrium oxide, as well as oxides of metals from the lanthanide series such as cerium and the related thorium oxide from the actinide series. Particularly preferred are mixed metal oxides having the structure of a spinel or a perovskite.

Where the composite material is intended for use as a catalyst in conversion of synthesis gas (syngas) to methanol or in the integrated conversion of syngas to olefins via the methanol, the co-catalyst can be at least one metal oxide capable of catalyzing the methanol synthesis reaction. A suitable methanol synthesis co-catalyst is copper oxide, typically in combination with an oxide of at least one element selected from the group consisting of silver, zinc, boron, magnesium, aluminum, vanadium, chromium, manganese, gallium, palladium, osmium, and zirconium. Preferably, the co-catalyst contains copper oxide and an oxide of at least one element selected from the group consisting of zinc, magnesium, aluminum, chromium, and zirconium. In one embodiment, the methanol synthesis catalyst is selected from the group consisting of copper oxides, zinc oxides, and aluminum oxides. More preferably, the catalyst contains oxides of copper and zinc.

Where the composite material is intended for use as a catalyst in reaction of ammonia with organic oxygenates, preferably methanol, to produce alkylamines, preferably methylamines, the co-catalyst can be at least one metal oxide capable of enhancing the selectivity and lifetime of the catalyst. Examples of suitable oxides include titanium oxide, lanthanum oxide, zirconium oxide, yttrium oxide, cerium oxide, thorium oxide, niobium oxide, chromium oxide, molybdenum oxide, ruthenium oxide, rhenium oxide, iron oxide, cobalt oxide, palladium oxide, copper oxide, zinc oxide, gallium oxide, indium oxide, tin oxide, bismuth oxide, nickel oxide, manganese oxide, kaolinite, dickite, nacrite, halloysite, montmorillonite, talc, mica, and illite.

In another embodiment, the methanol synthesis co-catalyst comprises copper oxide, zinc oxide, and at least one other oxide. Preferably, the at least one other oxide is selected from the group consisting of zirconium oxide, chromium oxide, vanadium oxide, magnesium oxide, aluminum oxide, titanium oxide, hafnium oxide, molybdenum oxide, tungsten oxide, and manganese oxide.

Whatever metal oxide is used as the co-catalyst, the oxide can be introduced into the meso- or macropores of the second framework structure in particulate form. More preferably, however, a solution containing a precursor of the or each metal oxide is impregnated into meso/macropores of the porous crystalline material and then the solution is treated with a precipitating agent, such as a base (for example, sodium hydroxide or ammonium hydroxide) to cause precipitation of the solid oxide material within the meso/macropores. Conveniently, the impregnation/precipitation is effected when a second set of pores are substantially free of any template or structure-directing agent used in the synthesis of the porous crystalline material, but the micropores are occupied by a structure-directing agent.

Another suitable co-catalyst for the composite material is a phosphorus-containing compound, normally a phosphorus oxide, since such materials are known to enhance the high temperature steam stability of silicate catalysts. Production of a phosphorus-containing co-catalyst can readily be accomplished by contacting the porous crystalline material with a solution of an appropriate phosphorus compound, followed by drying and calcining to convert the phosphorus to its oxide form. Contact with the phosphorus-containing solution is generally conducted at a temperature of about 25° C. and about 125° C. for a time between about 15 minutes and about 20 hours. After contacting with the phosphorus-containing solution, the porous crystalline material may be dried and calcined to convert the phosphorus to an oxide form. Calcination can be carried out in an inert atmosphere or in the presence of oxygen, for example, in air at a temperature of about 150 to 750° C., preferably about 300 to 500° C., for at least 1 hour, preferably 3-5 hours.

Representative phosphorus-containing compounds which may be used to incorporate a phosphorus oxide co-catalyst include derivatives of groups represented by $PX_3$, $RPX_2$, $R_2PX$, $R_3P$, $X_3PO$, $(XO)_3PO$, $(XO)_3P$, $R_3P=O$, $R_3P=S$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as phenyl radical, and X is hydrogen, R, or halide. These compounds include primary, $RPH_2$, secondary, $R_2PH$, and tertiary, $R_3P$, phosphines such as butyl phosphine, the tertiary phosphine oxides, $R_3PO$, such as tributyl phosphine oxide, the tertiary phosphine sulfides, $R_3PS$, the primary, $RP(O)(OX)_2$, and secondary, $R_2P(O)OX$, phosphonic acids such as benzene phosphonic acid, the corresponding sulfur derivatives such as $RP(S)(SX)_2$ and $R_2P(S)SX$, the esters of the phosphonic acids such as dialkyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites, and esters thereof such as the monopropyl ester, alkyl dialkylphosphinites, $(RO)PR_2$, and dialkyl alkyphosphinite, $(RO)_2PR$, esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$, and $(RS)_2PR$. Examples of phosphite esters include trimethylphosphite, triethylphosphite, diisopropylphosphite, butylphosphite, and pyrophosphites such as tetraethylpyrophosphite. The alkyl groups in the mentioned compounds preferably contain one to four carbon atoms.

Other suitable phosphorus-containing compounds include ammonium hydrogen phosphate, the phosphorus halides such as phosphorus trichloride, bromide, and iodide, alkyl phosphorodichloridites, $(RO)PCl_2$, dialkylphosphoro chloridites, $(RO)_2PCl$ dialkylphosphinochloroidites, $R_2PCl$, alkyl alkylphosphonochloridates, $(RO)(R)P(O)Cl$, dialkyl phosphinochloridates, $R_2P(O)Cl$, and $RP(O)Cl_2$. Applicable corresponding sulfur derivatives include $(RS)PCl_2$, $(RS)_2PCl$, $(RS)(R)P(S)Cl$, and $R_2P(S)Cl$.

Particular phosphorus-containing compounds include ammonium phosphate, ammonium dihydrogen phosphate, diammonium hydrogen phosphate, diphenyl phosphine chloride, trimethylphosphite, phosphorus trichloride, phosphoric acid, phenyl phosphine oxychloride, trimethylphosphate, diphenyl phosphinous acid, diphenyl phosphinic acid, diethylchlorothiophosphate, methyl acid phosphate, and other alcohol-P2O5 reaction products.

Conveniently, treatment with the phosphorus-containing compound is effected when the second set of pores are substantially free of any template or structure-directing agent used in the synthesis of the porous crystalline material, but the micropores are occupied by a structure-directing agent. Conversion of the phosphorus-containing compound into phosphorus oxide can then be carried out simultaneously with the removal of the structure-directing agent from the micropores or, alternatively, before or after removal of the structure-directing agent from the micropores.

A further desirable co-catalyst for the composite material is a hydrogenation-dehydrogenation component. Examples of such components include the oxide, hydroxide, sulfide, or free metal (i.e., zero valent) forms of Group 8 metals (i.e., Pt, Pd, Ir, Rh, Os, Ru, Ni, Co, and Fe), Group 6 metals (i.e, Cr, Mo, and W), Group 14 metals (i.e., Sn and Pb), Group 15 metals (i.e., Sb and Bi), and Group 7 metals (i.e., Mn, Tc, and Re). Combinations of catalytic forms of such noble or non-noble metal, such as combinations of Pt with Sn, may be used. The metal is preferably in a reduced valence state, e.g., when this component is in the form of an oxide or hydroxide. The reduced valence state of this metal may be attained, in situ, during the course of a reaction, when a reducing agent, such as hydrogen, is included in the feed to the reaction.

In one preferred embodiment of the invention, the hydrogenation-dehydrogenation component is a noble metal (i.e., Pt, Pd, Ir, Rh, Os, and Ru) and most preferably is platinum or palladium. In a further preferred embodiment of the invention, the hydrogenation-dehydrogenation component is an early transition metal, such as molybdenum, tungsten, rhenium and/or manganese, most preferably rhenium.

The hydrogenation/dehydrogenation component may be incorporated into the catalyst by methods known in the art, such as ion exchange, impregnation or physical admixture. For example, solutions of appropriate metal salts may be contacted with the remaining catalyst components, either before or after selectivation of the catalyst, under conditions sufficient to combine the respective components. The metal containing salt is preferably water soluble. Examples of such salts include chloroplatinic acid, tetraammineplatinum complexes, platinum chloride, tin sulfate, and tin chloride. The metal may be incorporated in the form of a cationic, anionic, or neutral complex such as $Pt(NH_3)_4^{2+}$ and cationic complexes of this type will be found convenient for exchanging metals onto the molecular sieve. For example, a platinum modified catalyst can be prepared by first adding the catalyst to a solution of ammonium nitrate in order to convert the catalyst to the ammonium form. The catalyst is subsequently contacted with an aqueous solution of tetraamine platinum (II) nitrate or tetraamine platinum(II) chloride. Anionic complexes such as the metatungstate, permanganate or perrhenate ions are also useful for impregnating metals onto the molecular sieves. After incorporation of the metal, the catalyst can then be filtered, washed with water and calcined at temperatures of from about 250 to about 500° C.

Conveniently, hydrogenation/dehydrogenation component is incorporated into the porous crystalline when the second set of pores are substantially free of any template or structure-directing agent used in the synthesis of the porous crystalline material, but the micropores are occupied by a structure-directing agent.

A further example of a suitable co-catalyst is a microporous molecular sieve having a framework structure different from said first framework structure. Examples of suitable molecular sieve co-catalysts include materials having the framework types MFI (e.g., ZSM-5 and silicalite-1), MEL (e.g., ZSM-11), MTW (e.g., ZSM-12), TON (e.g., ZSM-22), MTT (e.g., ZSM-23), FER (e.g., ZSM-35), MFS (e.g., ZSM-57), MWW (e.g., MCM-22, PSH-3, SSZ-25, ERB-1, ITQ-1, ITQ-2, ITQ-3, MCM-36, MCM-49, and MCM-56), IWR (e.g., ITQ-24), KFI (e.g., ZK-5), BEA (e.g., zeolite beta), ITH (e.g., ITQ-13), MOR (e.g., mordenite), FAU (e.g., zeolites X, Y, ultrastabilized Y, and dealuminized Y), LTL (e.g., zeolite L), IWW (e.g., ITQ-22), VFI (e.g., VPI-5), AEL (e.g., SAPO-11), AFI (e.g., ALPO-5), and AFO (SAPO-41), as well as materials such as MCM-68, EMM-1, EMM-2, ITQ-23, ITQ-24, ITQ-25, ITQ-26, ETS-2, ETS-10, SAPO-17, SAPO-34, and SAPO-35.

Provided the crystal size of the molecular sieve co-catalyst is sufficiently small the material can be introduced into meso/macropores of the composite material post-synthesis of the co-catalyst material. Alternatively, a synthesis mixture adapted to produce the desired molecular sieve co-catalyst can be introduced into the second set of pores and the co-catalyst material can be crystallized in situ in the composite material. In either case, introduction of the co-catalyst or its synthesis mixture is preferably conducted when the second set of pores are substantially free of any template or structure-directing agent used in the synthesis of the porous crystalline material, but the micropores are occupied by a structure-directing agent.

Uses of the Porous Composite Material

Examples of suitable catalytic uses of the porous composite material of the invention include (a) hydrocracking of heavy petroleum residual feedstocks, cyclic stocks and other hydrocrackate charge stocks, normally in the presence of a hydrogenation component selected from Groups 6 and 8 to 10 of the Periodic Table of Elements; (b) dewaxing, including isomerization dewaxing, to selectively remove straight chain paraffins from hydrocarbon feedstocks typically boiling above 177° C., including raffinates and lubricating oil basestocks; (c) catalytic cracking of hydrocarbon feedstocks, such as naphthas, gas oils, and residual oils, normally in the presence of a large pore cracking catalyst, such as zeolite Y; (d) oligomerization of straight and branched chain olefins having from about 2 to 21, preferably 2 to 5 carbon atoms, to produce medium to heavy olefins which are useful for both fuels, i.e., gasoline or a gasoline blending stock, and chemicals; (e) isomerization of olefins, particularly olefins having 4 to 6 carbon atoms, and especially normal butene to produce iso-olefins; (f) upgrading of lower alkanes, such as methane, to higher hydrocarbons, such as ethylene and benzene; (g) disproportionation of alkylaromatic hydrocarbons, such as toluene, to produce dialkylaromatic hydrocarbons, such as xylenes; (h) alkylation of aromatic hydrocarbons, such as benzene, with olefins, such as ethylene and propylene, to produce ethylbenzene and cumene; (i) isomerization of dialkylaromatic hydrocarbons, such as xylenes, (j) catalytic reduction of nitrogen oxides, and (k) synthesis of monoalkylamines and dialkylamines.

In addition, one particular use of the composite material of the invention is in the catalytic conversion of organic oxygenates to one or more olefins, particularly ethylene and propylene. As used herein, the term "organic oxygenates" is defined to include, but is not necessarily limited to aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety will normally contain from about 1 to about 10 carbon atoms, such as from about 1 to about 4 carbon atoms.

Representative organic oxygenates include lower straight chain or branched aliphatic alcohols, their unsaturated counterparts, and their nitrogen, halogen and sulfur analogues. Examples of suitable organic oxygenate compounds include methanol; ethanol; n-propanol; isopropanol; $C_4$-$C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines, n-alkyl halides, n-alkyl sulfides having n-alkyl groups of comprising the range of from about 3 to about 10 carbon atoms; and mixtures thereof. Particularly suitable oxygenate compounds are methanol, dimethyl ether, or mixtures thereof, most preferably methanol.

In the present oxygenate conversion process, a feedstock comprising an organic oxygenate, optionally, with one or more diluents, is contacted in the vapor phase in a reaction zone with a catalyst comprising the composite material of the present invention at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

When present, the diluent(s) is generally non-reactive to the feedstock or molecular sieve catalyst composition and is typically used to reduce the concentration of the oxygenate in the feedstock. Non-limiting examples of suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. Diluent(s) may comprise from about 1 mol % to about 99 mol % of the total feed mixture.

The temperature employed in the oxygenate conversion process may vary over a wide range, such as from about 200° C. to about 1000° C., for example, from about 250° C. to about 800° C., including from about 250° C. to about 750° C., conveniently from about 300° C. to about 650° C., typically from about 350° C. to about 600° C., and particularly from about 400° C. to about 600° C.

Light olefin products will form, although not necessarily in optimum amounts, at a wide range of pressures, including but not limited to autogenous pressures and pressures in the range of from about 0.1 kPa to about 10 MPa. Conveniently, the pressure is in the range of from about 7 kPa to about 5 MPa, such as in the range of from about 50 kPa to about 1 MPa. The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate; however, light olefins such as ethylene still may form.

The process should be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor) and the selected process design characteristics.

A wide range of weight hourly space velocities (WHSV) for the feedstock will function in the present process. WHSV is defined as weight of feed (excluding diluent) per hour per weight of a total reaction volume of molecular sieve catalyst (excluding inerts and/or fillers). The WHSV generally should be in the range of from about 0.01 $hr^{-1}$ to about 500 $hr^{-}$, such as in the range of from about 0.5 $hr^{-1}$ to about 300 $hr^{-1}$, for example, in the range of from about 0.1 $hr^{-1}$ to about 200 $hr^{-1}$.

A practical embodiment of a reactor system for the oxygenate conversion process is a circulating fluid bed reactor with continuous regeneration, similar to a modern fluid catalytic cracker. Fixed beds are generally not preferred for the process because oxygenate to olefin conversion is a highly exothermic process which requires several stages with intercoolers or other cooling devices. The reaction also results in a high pressure drop due to the production of low pressure, low density gas.

Because the catalyst must be regenerated frequently, the reactor should allow easy removal of a portion of the catalyst to a regenerator, where the catalyst is subjected to a regeneration medium, such as a gas comprising oxygen, for example, air, to burn off coke from the catalyst, which restores the catalyst activity. The conditions of temperature, oxygen partial pressure, and residence time in the regenerator should be selected to achieve a coke content on regenerated catalyst of less than about 0.5 wt %. At least a portion of the regenerated catalyst should be returned to the reactor.

In one embodiment, the catalyst is pretreated with dimethyl ether, a $C_2$-$C_4$ aldehyde composition and/or a $C_4$-$C_7$ olefin composition to form an integrated hydrocarbon co-catalyst within the porous framework of the CHA framework-type molecular sieve prior to the catalyst being used to convert oxygenate to olefins. Desirably, the pretreatment is conducted at a temperature of at least 10° C., such as at least 25° C., for example, at least 50° C., higher than the temperature used for the oxygenate reaction zone and is arranged to produce at least 0.1 wt %, such as at least 1 wt %, for example, at least about 5 wt % of the integrated hydrocarbon co-catalyst, based on total weight of the molecular sieve. Such preliminary treating to increase the carbon content of the molecular sieve is known as "pre-pooling" and is further described in U.S. Publication Nos. 2005-0101815; 2005-0101816; and 2005-0101817; all of which are incorporated herein by reference.

A further preferred use of the present composite material is in the conversion of syngas to methanol, either as a discrete and separate process or as part of an integrated process for converting syngas to olefins, with the entire process being effected by the porous inorganic oxide material and co-catalyst of the present composite catalyst. In a syngas conversion process, the syngas employed preferably has a molar ratio of hydrogen ($H_2$) to carbon oxides ($CO+CO_2$) in the range of from about 0.5:1 to about 20:1, preferably in the range of from about 2:1 to about 10:1. In another embodiment, the syngas has a molar ratio of hydrogen ($H_2$) to carbon monoxide (CO) of at least 2:1. Carbon dioxide is, optionally, present in an amount of not greater than 50% by weight, based on total weight of the syngas. Desirably, the syngas contains $CO_2$ and CO at a molar ratio of from about 0.5 to about 1.2, preferably from about 0.6 to about 1.0.

The methanol synthesis process is effective over a wide range of temperatures. In one embodiment, the syngas is contacted with the methanol synthesis catalyst at a temperature in the range of from about 302° F. (150° C.) to about 842° F. (450° C.), preferably in a range of from about 347° F. (175° C.) to about 662° F. (350° C.), more preferably in a range of from about 392° F. (200° C.) to about 572° F. (300° C.). The process is also operable over a wide range of pressures. In one embodiment, the syngas is contacted with the methanol synthesis catalyst at a pressure in the range of from about 15 atmospheres to about 125 atmospheres, preferably in a range of from about 20 atmospheres to about 100 atmospheres, more preferably in a range of from about 25 atmospheres to about 75 atmospheres. Gas hourly space velocities vary depending upon the type of continuous process that is used. Desirably, gas hourly space velocity of flow of gas through the catalyst bed is in the range of from about 50 $hr^{-1}$ to about 50,000 $hr^{-1}$. Preferably, gas hourly space velocity of flow of gas through the catalyst bed is in the range of from about 250 $hr^{-1}$ to about 25,000 $hr^{-1}$, more preferably from about 500 $hr^{-1}$ to about 10,000 $hr^{-1}$.

Another particular use of the composite material of the invention is in the reaction of organic oxygenates with ammonia to produce monoalkylamines and dialkylamines, particularly methylamine and dimethylamine. Examples of suitable organic oxygenate compounds for use in this reaction include alcohols having 1 to 3 carbon atoms, specifically, methanol, ethanol, n-propanol and isopropanol, and their ether counterparts, including methyl ethyl ether, dimethyl ether, diethyl ether, and di-isopropyl ether. The reaction is conducted, preferably but not exclusively, in a flowing system in a gaseous fixed bed or fluidized bed, with the molar ratio of ammonia to oxygenate being generally from about 0.5 to about 20, such as about 1 to about 5. The reaction conditions typically include a temperature of about 200 to 400° C., such as about 250 to about 360° C., a pressure of about 0.1 to about 10 MPa, such as about 0.5 to about 2 MPa and gas hourly space velocity, GHSV, of about 100 to about 10,000 $hr^{-1}$.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for converting a starting material into a product, the process comprising contacting the staffing material with a catalyst comprising a porous, composite material, which comprises:
   (a) providing a porous crystalline inorganic oxide material comprising a first framework structure defining a first set of micropores and comprising a second framework structure defining a second set of mesopores or macropores, wherein said micropores are occupied by a structure-directing agent, and said second set of pores are substantially free of structure-directing agent;
   (b) introducing a co-catalyst precursor in the second set of pores of said inorganic oxide material;
   (c) transforming the co-catalyst precursor into a co-catalyst; and
   (d) removing the structure directing agent from the micropores of the inorganic oxide material;
      (i) wherein the porous crystalline inorganic oxide material comprises a first framework structure defining a first set of uniformly distributed pores having an average cross-sectional dimension of from 0.3 to less than 2 nanometers and comprising a second framework structure defining a second set of uniformly distributed pores having an average cross-sectional dimension of from 2 to 200 nanometers; and
      (ii) the co-catalyst is selected from one or more of (1) at least one metal oxide different from said inorganic oxide material, (2) a phosphorus-containing compound, (3) a hydrogenation-dehydrogenation component, and (4) a microporous molecular sieve having a framework structure different from said first framework structure.

2. The process of claim 1, wherein said starting material is synthesis gas and the process is conversion of synthesis gas into methanol and/or olefins.

3. The process of claim 1, wherein said starting material is an organic oxygenate and the process is conversion of the organic oxygenate into olefins.

4. The process of claim 1, wherein said staffing material is an organic oxygenate and the process is the reaction of the organic oxygenate with ammonia to produce alkylamines.

5. A process for converting a staffing material into a product comprising:
   (a) providing a porous crystalline inorganic oxide material comprising a first framework structure defining a first set of micropores and comprising a second framework structure defining a second set of mesopores or macropores, wherein said micropores are occupied by a structure-directing agent, and said second set of pores are substantially free of structure-directing agent;
   (b) introducing a co-catalyst precursor in the second set of pores of said inorganic oxide material, wherein the co-catalyst precursor is selected from one or more of (a) at least one metal oxide different from said inorganic oxide material, (b) a phosphorus-containing compound, (c) a hydrogenation-dehydrogenation component and (d) a microporous molecular sieve having a framework structure different from said first framework structure;
   (c) transforming the co-catalyst precursor into a co-catalyst;
   (d) removing the structure directing agent from the micropores of the inorganic oxide material, thus forming a catalyst comprising a porous, composite material; and
   (e) contacting the starting material with the catalyst comprising a porous, composite material under conditions sufficient to at least partially convert the staffing material into the product.

6. The process of claim 5, wherein the first set of micropores have an average cross-sectional dimension of from 0.3 to less than 2 nanometers the second set of mesopores or macropores have an average cross-sectional dimension of from 2 to 200 nanometers.

* * * * *